(12) United States Patent
DeHennis

(10) Patent No.: US 10,713,208 B2
(45) Date of Patent: *Jul. 14, 2020

(54) REMOTELY POWERED, MULTISITE SENSING SYSTEM WITH A SHARED, TWO-WIRE BUS FOR POWER AND COMMUNICATION

(71) Applicant: Senseonics, Incorporated, Germantown, MD (US)

(72) Inventor: Andrew DeHennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,220

(22) Filed: Jun. 4, 2019

(65) Prior Publication Data
US 2019/0294580 A1    Sep. 26, 2019

Related U.S. Application Data

(63) Continuation of application No. 16/105,596, filed on Aug. 20, 2018, now Pat. No. 10,318,472, which is a (Continued)

(51) Int. Cl.
*G06F 13/42* (2006.01)
*G06F 13/28* (2006.01)
(Continued)

(52) U.S. Cl.
CPC ......... *G06F 13/4282* (2013.01); *G01N 33/50* (2013.01); *G06F 1/3209* (2013.01);
(Continued)

(58) Field of Classification Search
CPC .. G06F 13/4282; G06F 1/3209; G06F 13/404; G06F 13/287; H04B 5/0075;
(Continued)

(56) References Cited

U.S. PATENT DOCUMENTS 4,203,096 A    5/1980  Farley et al.
6,561,978 B1   5/2003  Conn et al.
(Continued)

OTHER PUBLICATIONS

Colvin et al "Increased in vivo stability and functional lifetime of an implantable glucose sensor through platinum catalysis", Journal of Biomedical Materials Research Part A, vol. 101A, Issue 5, pp. 1274-1282, Oct. 15, 2012.

*Primary Examiner* — Dennis White
(74) *Attorney, Agent, or Firm* — Rothwell, Figgs, Ernst & Manbeck, P.C.

(57) ABSTRACT

A multisite sensing system including two or more analyte sensors, an interface device, and a shared bus. The interface device may be configured to receive a power signal and generate power for powering the analyte sensors and to convey data signals generated by the analyte sensors. The shared bus connected to the interface device and each of the analyte sensors and configured to provide the power generated by the interface device to the analyte sensors and to provide the data signals generated by the analyte sensors to the interface device. The interface device may be an inductive element. The shared bus may be a two wire, multiplexed bus. The analyte sensors may be spatially separated for analyte sensing at least two different locations. The analyte sensors may generate data signals indicative of the presence and/or amount of the same analyte or of one or more different analytes.

19 Claims, 1 Drawing Sheet

Related U.S. Application Data continuation of application No. 15/482,141, filed on Apr. 7, 2017, now Pat. No. 10,102,178, which is a continuation of application No. 14/594,674, filed on Jan. 12, 2015, now Pat. No. 9,626,315.

(60) Provisional application No. 61/926,636, filed on Jan. 13, 2014.

(51) Int. Cl.
*G01N 33/50* (2006.01)
*H04B 5/00* (2006.01)
*H02J 50/10* (2016.01)
*G06F 1/3209* (2019.01)
*G06F 13/40* (2006.01)

(52) U.S. Cl.
CPC .......... *G06F 13/287* (2013.01); *G06F 13/404* (2013.01); *H02J 50/10* (2016.02); *H04B 5/0037* (2013.01); *H04B 5/0075* (2013.01); *Y02D 10/14* (2018.01); *Y02D 10/151* (2018.01)

(58) Field of Classification Search
CPC ....... H04B 5/0037; H02J 50/10; G01N 33/50; Y02D 10/14; Y02D 10/151
See application file for complete search history.

(56) References Cited

U.S. PATENT DOCUMENTS

| | | |
|---|---|---|
| 6,960,987 B2 | 11/2005 | Dohi et al. |
| 2002/0072785 A1 | 6/2002 | Nelson et al. |
| 2003/0122677 A1 | 7/2003 | Kail, IV |
| 2008/0092638 A1 | 4/2008 | Brenneman et al. |
| 2008/0119707 A1 | 5/2008 | Stafford |
| 2008/0154101 A1 | 6/2008 | Jain et al. |
| 2009/0054737 A1 | 2/2009 | Magar et al. |
| 2010/0073669 A1 | 3/2010 | Colvin, Jr. et al. |
| 2010/0230614 A1 | 9/2010 | Lear et al. |
| 2010/0312483 A1 | 12/2010 | Peyser et al. |
| 2011/0034912 A1 | 2/2011 | de Graff et al. |
| 2012/0028820 A1 | 2/2012 | Rhodes et al. |
| 2013/0211213 A1 | 8/2013 | DeHennis et al. |
| 2014/0257059 A1 | 9/2014 | Budiman et al. |
| 2015/0199288 A1 | 7/2015 | DeHennis |

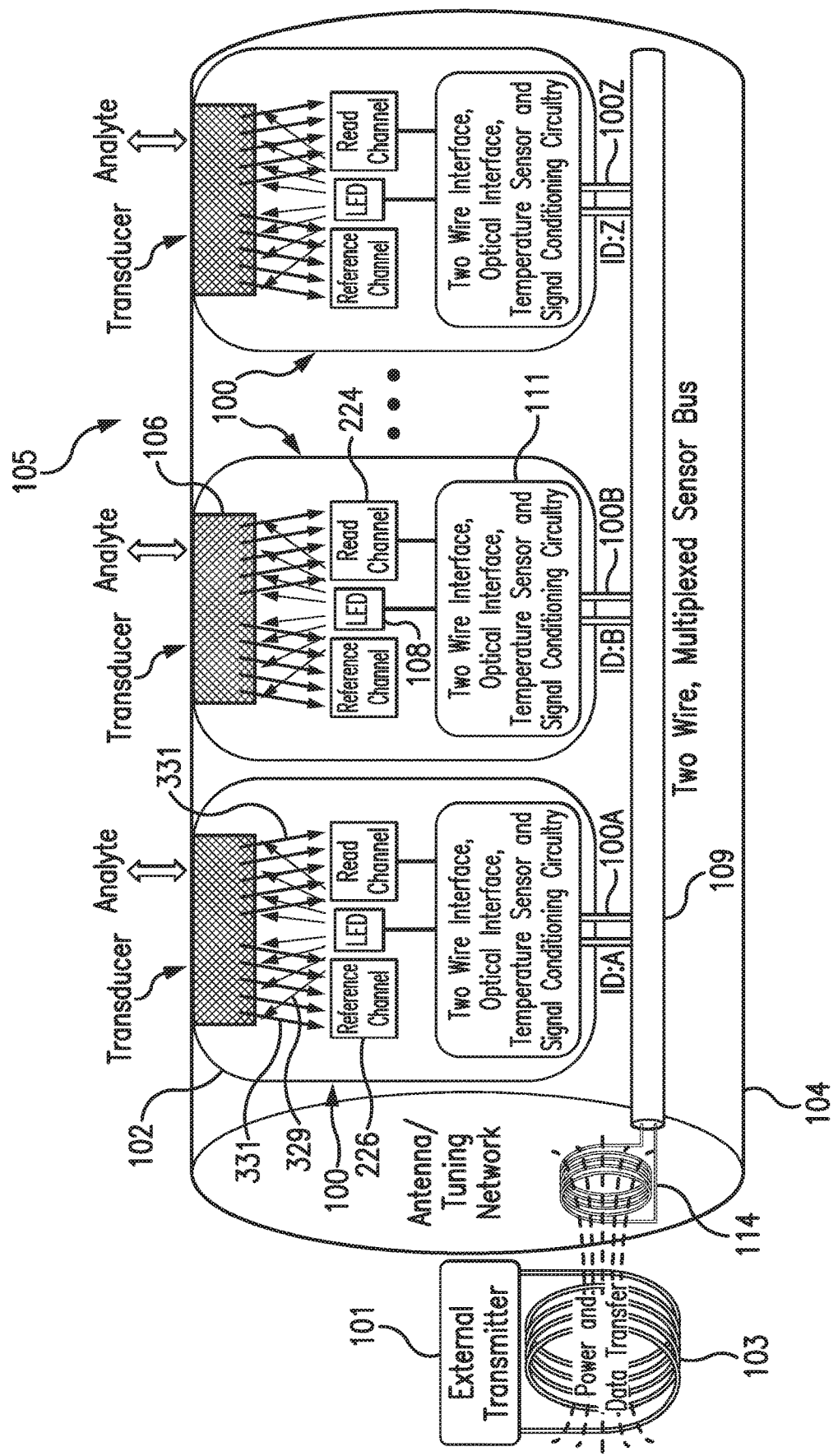

REMOTELY POWERED, MULTISITE SENSING SYSTEM WITH A SHARED, TWO-WIRE BUS FOR POWER AND COMMUNICATION

CROSS-REFERENCE TO RELATED APPLICATION

This application is a continuation of U.S. patent application Ser. No. 16/105,596, which was filed on Aug. 20, 2018, and is a continuation of U.S. patent application Ser. No. 15/482,141, which was filed on Apr. 7, 2017, now U.S. Pat. No. 10,102,178, and is a continuation of U.S. patent application Ser. No. 14/594,674, which was filed on Jan. 12, 2015, now U.S. Pat. No. 9,626,315, and claims the benefit of priority to U.S. Provisional Application Ser. No. 61/926,636, filed on Jan. 13, 2014, all of which are incorporated herein by reference in their entireties.

BACKGROUND

Field of Invention

The present invention relates generally to a multisite sensing system with a shared bus. Specifically, the present invention may relate to a remotely powered, multisite sensing system with a shared, two-wire bus for power and communication.

Discussion of the Background

A conventional implantable analyte sensor may include a single analyte sensing site and an antenna that is inductively coupled to an external transceiver and used solely with the single analyte sensing site. Such a sensor, when implanted, may provide good telemetry coupling with an external transceiver that is worn on the outside of the skin directly over the implanted sensor. However, the sensor only has one analyte sensing site and is dependent upon having an antenna that can receive power and commands from the external transceiver at the same location as the sensing site. These requirements (i.e., only one sensing site and one antenna per sensing site) may limit the range of applications to which the sensor may be applied. There is presently a need in the art for a multisite sensing system.

SUMMARY

The present invention overcomes the disadvantages of prior systems by providing a multisite sensing system. The multisite sensing system may provide, among other advantages, multiple analyte sensing sites and a single interface device (e.g., antenna) that is shared between the multiple sensing sites. The multiple sensing sites may include two or more sensing sites that detect the same analyte (e.g., for secondary, tertiary, or more detection of the analyte) and/or one or more sensing sites that each detect an analyte different than the analyte(s) detected by the other sensing site(s) (e.g., for detection of multiple analytes). In addition, in some embodiments, the multisite sensing system may include a shared bus (e.g., a two wire interface), which may simplify the overall assembly and form factor.

One aspect of the invention may provide a multisite sensing system including two or more analyte sensors, an interface device, and a shared bus. The interface device may be configured to receive a power signal and generate power for powering the two or more analyte sensors and to convey data signals generated by the two or more analyte sensors. The shared bus connected to the interface device and each of the two or more sensors and configured to provide the power generated by the interface device to the two or more analyte sensors and to provide the data signals generated by the two or more analyte sensors to the interface device.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGURE is a schematic view illustrating a multisite sensing system embodying aspects of the present invention.

DETAILED DESCRIPTION OF PREFERRED EMBODIMENTS

FIGURE is a schematic view of a multisite sensing system 105 embodying aspects of the present invention. As illustrated in FIGURE, the multisite sensing system 105 may include a plurality of analyte sensors 100, a system housing 104, and shared bus 109. In some non-limiting embodiments, the multisite sensing system 105 may be a fully implantable multisite analyte sensing system. The multisite sensing system 105 may be implanted in a living animal (e.g., a living human). The multisite sensing system 105 may be implanted, for example, in a living animal's arm, wrist, leg, abdomen, peritoneum, intravenously, or other region of the living animal suitable for sensor implantation. For example, in one non-limiting embodiment, the multisite sensing system 105 may be implanted beneath the skin (i.e., in the subcutaneous or peritoneal tissues). In some embodiments, the multisite sensing system 105 may be implanted subcutaneously (e.g., in a location of the body that is appropriate for subcutaneous measurement of interstitial fluid glucose), and no portion of the sensor 100 protrudes from the skin. In some non-limiting embodiments, the multisite sensing system 105 may be capable of being continuously implanted for at least 90 days or longer and may be replaced thereafter.

In some embodiments, the multisite sensing system 105 may include two or more analyte sensors 100. For example, in the embodiment illustrated in FIGURE, the system 105 includes sensors 100A, 100B, and 100Z, but the system 105 may include any number of sensors 100 greater than or equal to two (e.g., two, three, four, five, ten, etc.). The analyte sensors 100 may detect the presence, amount, and/or concentration of an analyte (e.g., glucose, oxygen, cardiac markers, low-density lipoprotein (LDL), high-density lipoprotein (HDL), or triglycerides). In some embodiments, two or more of the sensors 100 may detect the same analyte. In some non-limiting embodiments where two or more of the sensors 100 detect the same analyte, a voting scheme (e.g., taking an integrated average of the measurements from the sensors detecting the same analyte and/or discounting a measurement that is significantly different than other measurements of the same analyte) may be used (e.g., by the transceiver 101). In some embodiments, one or more of the sensors 100 may detect a first analyte, and another one or more sensors 100 may detect a second, different analyte. In some embodiments, sensors 100 may additionally detect third, fourth, and/or more different analytes. In some embodiments, the sensors 100 are spatially separated for analyte detection at multiple locations. In some non-limiting embodiments, the analyte sensors 100 may be optical sensors (e.g., fluorometers). In some embodiments, the sensors 100 may be chemical or biochemical sensors.

The multisite sensing system 105 may communicate with an external transceiver 101. The transceiver 101 may be an electronic device that communicates with the multisite sensing system 105 to power the sensors 100 and/or receive measurement information (e.g., photodetector and/or temperature sensor readings) from the sensors 100. The measurement information may include one or more readings from one or more photodetectors of the sensors 100 and/or one or more readings from one or more temperature sensors of the sensors 100. In some embodiments, the transceiver 101 may calculate analyte concentrations from the measurement information received from the sensor 100. However, it is not required that the transceiver 101 perform the analyte concentration calculations itself, and, in some alternative embodiments, the transceiver 101 may instead convey/relay the measurement information received from the sensor 100 to another device for calculation of analyte concentrations.

In some embodiments (e.g., embodiments in which the multisite sensing system 105 is a fully implantable multisite sensing system), the transceiver 101 may implement a passive telemetry for communicating with the implantable sensor 100 via an inductive magnetic link for both power and data transfer. The multisite sensing system 105 may include an inductive element 114, which may be, for example, a ferrite based micro-antenna. In some embodiments, the inductive element 114 may be connected to analyte detection circuitry. For example, in some embodiments, where the sensors 100 are optical sensors, the inductive element 114 may be connected to micro-fluorimeter circuitry (e.g., an application specification integrated circuit (ASIC)) and a related optical detection system of the sensor 100. In some embodiments, the sensor 100 may not include a battery, and, as a result, the multisite sensing system 105 may rely on the transceiver 101 to provide power for the sensors 100 and a data link to convey analyte-related data from the sensors 100 to transceiver 101.

In some non-limiting embodiments, the multisite sensing system 105 may be a passive, fully implantable multisite sensing system having a small size. For a multisite sensing system 105 that is a fully implantable multisite sensing system having no battery power source, the transceiver 101 may provide energy to run the sensors 100 of the multisite sensing system 105 via a magnetic field. In some embodiments, the magnetic transceiver-sensing system link can be considered as "weakly coupled transformer" type. The magnetic transceiver-sensing system link may provide energy and a link for data transfer using amplitude modulation (AM). Although in some embodiments, data transfer is carried out using AM, in alternative embodiments, other types of modulation may be used. The magnetic transceiver-sensor link may have a low efficiency of power transfer and, therefore, may require relatively high power amplifier to energize the sensors 100 of the multisite sensing system 105 at longer distances. In some non-limiting embodiments, the transceiver 101 and multisite sensing system 105 may communicate using near field communication (e.g., at a frequency of 13.56 MHz, which can achieve high penetration through the skin and is a medically approved frequency band) for power transfer. However, this is not required, and, in other embodiments, different frequencies may be used for powering and communicating with the sensor 100.

In some embodiments, as illustrated in FIGURE, the transceiver 101 may include an inductive element 103, such as, for example, a coil. The transceiver 101 may generate an electromagnetic wave or electrodynamic field (e.g., by using a coil) to induce a current in an inductive element 114 of the multisite sensing system 105, which powers the sensors 100. The transceiver 101 may also convey data (e.g., commands) to the sensors 100 of the multisite sensing system 105. For example, in a non-limiting embodiment, the transceiver 101 may convey data by modulating the electromagnetic wave used to power the sensors 100 (e.g., by modulating the current flowing through a coil 103 of the transceiver 101). The modulation in the electromagnetic wave generated by the transceiver 101 may be detected/extracted by the sensors 100. Moreover, the transceiver 101 may receive data (e.g., measurement information) from the sensors 100 of the multisite sensing system 105. For example, in a non-limiting embodiment, the transceiver 101 may receive data by detecting modulations in the electromagnetic wave generated by one or more of the sensors 100, e.g., by detecting modulations in the current flowing through the coil 103 of the transceiver 101.

The inductive element 103 of the transceiver 101 and the inductive element 114 of the multisite sensing system 105 may be in any configuration that permits adequate field strength to be achieved when the two inductive elements are brought within adequate physical proximity.

In some embodiments, the multisite sensing system 105 includes a shared bus 109 connected to the inductive element 114 and to each of the sensors 100. In some non-limiting embodiments, the bus 109 may be a multiplexed bus. In some non-limiting embodiments, the bus 109 may be a two wire, multiplexed bus. For example, in one non-limiting embodiment, the shared bus 109 may consist of two wires connected to the inductive element 114. A first wire of the shared bus 109 may be connected to a first end of the inductive element 114 and to a first input/output port (e.g., a pin) of each of the sensors 100, and a second wire of the shared bus 109 may be connected to a second end of the inductive element 114 and to a second input/output port (e.g., a pin) of each of the sensors 100. In some non-limiting embodiments, the first and second input/output ports may be resonant nodes of an LC tank circuit. In some embodiments, the shared bus 109 delivers the power generated by the inductive element 114 to each of the sensors 100. In some embodiments, the connection of the shared bus 109 to the inductive element 114 facilitates data communication between the sensors 100 and the transceiver 101.

In some non-limiting embodiments, multiplexing may be performed using address mode communication features of the sensors 100 (e.g., address mode communication features of bus interface circuitry included in the circuit components 111 of the sensors 100). In some embodiments, measurement commands conveyed by the inductive element 103 of the transceiver 101 (e.g., by modulating the electromagnetic wave) may include an address (e.g., a unique sensor ID) identifying a particular one of the sensors 100, and the address mode communication features of the sensors 100 may extract the address in the conveyed measurement commands. In some embodiments, only the sensor 100 to which the measurement command is addressed (e.g., only the sensor 100 whose unique ID matches the unique ID included in the measurement command) performs a measurement and provides a response through the passive interface (e.g., by modulating in the electromagnetic wave). In this way, sensors 100 connected to the shared bus 109 may operate in a multiplexed fashion. Although one example for multiplexed operation of the sensors 100 is provided above, alternative embodiments may achieve multiplexed sensor operation in one or more different fashions. For example, in some alternative embodiments, the sensors 100 may be configured to use an anti-collision algorithm for multiplexing the response on the shared antenna 114. In some non-limiting embodiments, the two wires of the shared bus 109 may enable the single inductive element 114 (e.g., a single antenna) to interface with multiple sensors 100, which may be spatially separated for analyte detection/transduction at multiple locations.

In some non-limiting embodiments, as illustrated in FIGURE, the sensors 100, shared bus 109, and inductive element 114 may be encased in a system housing 104 (i.e., body, shell, capsule, or encasement), which may be rigid and biocompatible. In one non-limiting embodiment, the system housing 104 may be a silicon tube. However, this is not required, and, in other embodiments, different materials and/or shapes may be used for the system housing 104.

The sensors 100 may include a transmissive optical cavity 102. In some non-limiting embodiments, the transmissive optical cavity 102 may be formed from a suitable, optically transmissive polymer material, such as, for example, acrylic polymers (e.g., polymethylmethacrylate (PMMA)). However, this is not required, and, in other embodiments, different materials may be used for the transmissive optical cavity 102.

In some embodiments, the sensors 100 may include an analyte indicator element 106, such as, for example, a polymer graft coated, diffused, adhered, or embedded on or in at least a portion of the exterior surface of the system housing 104. The analyte indicator element 106 (e.g., polymer graft) of the sensor 100 may include indicator molecules (e.g., fluorescent indicator molecules) exhibiting one or more detectable properties (e.g., optical properties) based on the amount or concentration of the analyte in proximity to the analyte indicator element. In some embodiments, the sensors 100 may include a light source 108 that emits excitation light 329 over a range of wavelengths that interact with the indicator molecules in the analyte indicator element 106. The sensors 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules of the analyte indicator element 106 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflected excitation light) and reflect the remaining wavelengths. In some non-limiting embodiments, the sensors 100 may include a temperature transducer. In some non-limiting embodiments, the multisite sensing system 105 may include a drug-eluting polymer matrix that disperses one or more therapeutic agents (e.g., an anti-inflammatory drug).

In some embodiments, the sensors 100 may include circuit components 111. In some non-limiting embodiments, the circuit components 111 may include a bus interface, optical interface, temperature sensor, analog-to-digital converter, and/or signal conditioning circuitry. In some non-limiting embodiments, the bus interface may perform the address mode communication described above. In some of these address mode communication embodiments, all of the sensors 100 may receive a measurement command, and only the sensor 100 to which the measurement command is addressed responds to the measurement command via the bus 109 and shared inductive element 114.

In some embodiments, the sensors 100 may include a substrate. In some embodiments, the substrate may be a circuit board (e.g., a printed circuit board (PCB) or flexible PCB) on which one or more of circuit components 111 (e.g., analog and/or digital circuit components) may be mounted or otherwise attached. However, in some alternative embodiments, the substrate may be a semiconductor substrate having one or more of the circuit components 111 fabricated therein. For instance, the fabricated circuit components may include analog and/or digital circuitry. Also, in some semiconductor substrate embodiments, in addition to the circuit components fabricated in the semiconductor substrate, circuit components may be mounted or otherwise attached to the semiconductor substrate. In other words, in some semiconductor substrate embodiments, a portion or all of the circuit components 111, which may include discrete circuit elements, an integrated circuit (e.g., an application specific integrated circuit (ASIC)) and/or other electronic components (e.g., a non-volatile memory), may be fabricated in the semiconductor substrate with the remainder of the circuit components 111 is secured to the semiconductor substrate, which may provide communication paths between the various secured components.

In some embodiments, the one or more of the analyte indicator element 106, light source 108, photodetectors 224, 226, circuit components 111, and substrate of the sensors 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, and U.S. application Ser. No. 14/142,017, filed on Dec. 27, 2013, all of which are incorporated by reference in their entireties. Similarly, the structure, function, and/or features of the system housing 104, sensors 100, and/or transceiver 101 may be as described in one or more of U.S. application Ser. Nos. 13/761,839, 13/937,871, 13/650,016, and 14/142,017. For instance, the system housing 104 may have one or more hydrophobic, hydrophilic, opaque, and/or immune response blocking membranes or layers on the exterior thereof.

Although in some embodiments, as illustrated in FIGURE, the sensors 100 may be an optical sensors, this is not required, and, in one or more alternative embodiments, sensors 100 may be a different types of analyte sensors, such as, for example, diffusion sensors or pressure sensors. Also, although in some embodiments, as illustrated in FIGURE, the multisite sensing system 105 may be a fully implantable sensing system, this is not required, and, in some alternative embodiments, the multisite sensing system 105 may be a transcutaneous sensing system having a wired connection to the transceiver 101. For example, in some alternative embodiments, the sensing system 105 may be located in or on a transcutaneous needle (e.g., at the tip thereof). In these embodiments, instead of wirelessly communicating using inductive elements 103 and 114, the multisite sensing system 105 and transceiver 101 may communicate using one or more wires connected between the transceiver 101 and the transceiver transcutaneous needle that includes the multisite sensing system 105. For another example, in some alternative embodiments, the multisite sensing system 105 may be located in a catheter (e.g., for intravenous blood glucose monitoring) and may communicate (wirelessly or using wires) with the transceiver 101.

In some embodiments, the multisite sensing system 105 may include a transceiver interface device. In some embodiments where the multisite sensing system 105 includes an antenna (e.g., inductive element 114), the transceiver interface device may include the antenna (e.g., inductive element 114) of multisite sensing system 105. In some of the transcutaneous embodiments where there exists a wired connection between the multisite sensing system 105 and the transceiver 101, the transceiver interface device may include the wired connection.

Embodiments of the present invention have been fully described above with reference to the drawing FIGURES. Although the invention has been described based upon these preferred embodiments, it would be apparent to those of skill in the art that certain modifications, variations, and alternative constructions could be made to the described embodiments within the spirit and scope of the invention.

What is claimed is:

1. A sensing system comprising:
a first sensor configured to generate a first data signal;
a second sensor configured to generate a second data signal, wherein the first and second sensor are spatially separated;
an interface device configured to convey the first and second data signals to a transceiver external to the sensing system; and
a shared bus (a) connected to the interface device, the first sensor, and the second sensor and (b) configured to provide the first and second data signals from the first and second sensors to the interface device.

2. The sensing system of claim 1, wherein the shared bus is a multiplexed bus.

3. The sensing system of claim 1, further comprising a third sensor configured to generate a third data signal, wherein the first, second, and third sensors are spatially separated.

4. The sensing system of claim 1, wherein the interface device is an inductive element.

5. The sensing system of claim 1, wherein the first sensor comprises a light source and a light detector.

6. The sensing system of claim 1, wherein first sensor comprises a substrate and one or more circuit components fabricated in or mounted on the substrate.

7. The sensing system of claim 1, further comprising a housing containing the first and second sensors, shared bus, and interface device.

8. The sensing system of claim 7, wherein the first sensor comprises a first analyte indicator embedded within and/or covering at least a first portion of the housing, the second sensor comprises a second analyte indicator embedded within and/or covering at least a second portion of the housing, and the first and second portions of the housing are separate portions of the housing.

9. The sensing system of claim 1, wherein the shared bus consists of two wires each connected to the interface device, the first sensor, and the second sensor.

10. The sensing system of claim 1, wherein the first sensor comprises a first analog-to-digital converter, and the second sensor comprises a second analog-to-digital converter.

11. The sensing system of claim 1, wherein the shared bus comprises two wires each connected to the interface device, the first sensor, and the second sensor.

12. A method comprising:
using a first sensor of a sensing system to generate a first data signal;
using a second sensor of the sensing system to generate a second data signal, wherein the second sensor and the first sensor are spatially separated;
using a shared bus of the sensing system to provide the first and second data signals from the first and second sensors to an interface device of the sensing system, wherein the shared bus is connected to the interface device, the first sensor, and the second sensor; and
using the interface device to convey the first and second data signals to a transceiver external to the sensing system.

13. The method of claim 12, further comprising using a third sensor of the sensing system to generate a third data signal, wherein the first, second, and third sensors are spatially separated.

14. A method comprising:
using two wires of a shared bus of a sensing system to provide data signals generated by two or more analyte sensors of the sensing system to an interface device of the sensing system, wherein the shared bus is connected to the interface device and each of the two or more analyte sensors; and
using an interface device to convey data signals generated by the two or more analyte sensors.

15. A method comprising:
using an interface device of a sensing system to receive a command from a transceiver external to the sensing system, wherein the command includes an address;
using a shared bus of the sensing system to provide the command received by the interface device to first and second sensors of the sensing system, wherein the shared bus is connected to the interface device, the first sensor, and the second sensor;
using the first sensor of the sensing system to extract the address from the command, determine that the extracted address matches a first address, and generate a response to the command;
using the second sensor of the sensing system to extract the address from the command, determine that the extracted address does not match a second address, and not provide a response to the command, wherein the first address is different than the second address;
using the shared bus to provide the response generated by the first sensor to the interface device; and
using the interface device to convey the response generated by the first sensor to the transceiver.

16. The method of claim 15, further comprising:
using the interface device to receive another command from the transceiver external to the sensing system, wherein the command includes another address;
using the shared bus to provide the other command received by the interface device to the first and second sensors;
using the first sensor to extract the other address from the other command, determine that the extracted other address does not match the first address, and not provide a response to the other command;
using the second sensor to extract the other address from the other command, determine that the extracted other address matches the second address, and generate a response to the other command;

using the shared bus to provide the response generated by the second sensor to the interface device; and using the interface device to convey the response generated by the second sensor to the transceiver.

17. The method of claim 15, further comprising:

using the interface device to receive power from the transceiver and generate a current; and using the shared bus to provide the current generated by the interface device to the first and second sensors;

wherein the first analyte sensor and the second analyte sensor extract the address from modulations in the current generated by the interface device, and the first and second sensors are powered by the current generated by the interface device.

18. The method of claim 15, wherein the shared bus consists of two wires each connected to the interface device, the first sensor, and the second sensor.

19. The method of claim 15, wherein the shared bus comprises two wires each connected to the interface device, the first sensor, and the second sensor.

* * * * *